United States Patent [19]
Kumar

[11] Patent Number: 6,149,841
[45] Date of Patent: Nov. 21, 2000

[54] PHOTOCHROMIC BENZOPYRANO-FUSED NAPHTHOPYRANS

[75] Inventor: Anil Kumar, Pittsburgh, Pa.

[73] Assignee: PPG Industries Ohio, Inc., Cleveland, Ohio

[21] Appl. No.: 09/466,704

[22] Filed: Dec. 17, 1999

Related U.S. Application Data

[63] Continuation-in-part of application No. 09/114,089, Jul. 10, 1998, Pat. No. 6,022,495.

[51] Int. Cl.$^7$ ............................. G02B 5/23; C07D 311/78
[52] U.S. Cl. .......................... 252/586; 549/382; 549/275; 549/58; 549/60; 549/337; 549/362; 544/124; 544/148; 544/150; 546/167; 546/194; 546/196; 546/197; 546/280.7; 546/281.1; 546/284.1; 548/454; 548/518; 548/525; 548/526; 351/163
[58] Field of Search ............................ 252/586; 549/382, 549/275, 58, 60, 337, 362; 544/124, 148, 150; 546/167, 194, 196, 197, 280.7, 281.1, 284.1; 548/454, 518, 525, 526; 351/163

[56] References Cited

U.S. PATENT DOCUMENTS

| | | | |
|---|---|---|---|
| 3,567,605 | 3/1971 | Becker | 252/586 |
| 3,627,690 | 12/1971 | Casella et al. | 252/586 |
| 4,818,096 | 4/1989 | Heller | 351/163 |
| 5,066,818 | 11/1991 | Van Gemert et al. | 549/382 |
| 5,429,774 | 7/1995 | Kumar | 549/382 |
| 5,458,814 | 10/1995 | Kumar et al. | 252/586 |
| 5,514,817 | 5/1996 | Knowles | 252/586 |
| 5,552,091 | 9/1996 | Kumar | 252/586 |
| 5,565,147 | 10/1996 | Knowles et al. | 252/586 |
| 5,651,923 | 7/1997 | Kumar et al. | 252/586 |
| 5,674,432 | 10/1997 | Knowles et al. | 252/586 |
| 5,723,072 | 3/1998 | Kumar | 252/586 |
| 5,869,658 | 2/1999 | Lin et al. | 252/586 |

*Primary Examiner*—Philip Tucker
*Attorney, Agent, or Firm*—Irwin M. Stein; Frank P. Mallak

[57] ABSTRACT

Described are novel photochromic benzopyrano-fused naphthopyran compounds, examples of which are naphthopyran compounds having a substituted or unsubstituted benzopyran group fused to one side of the naphtho portion of the naphthopyran and having certain substituents at the position ortho to the oxygen atom of the naphthopyran ring. These compounds may be represented by the following:

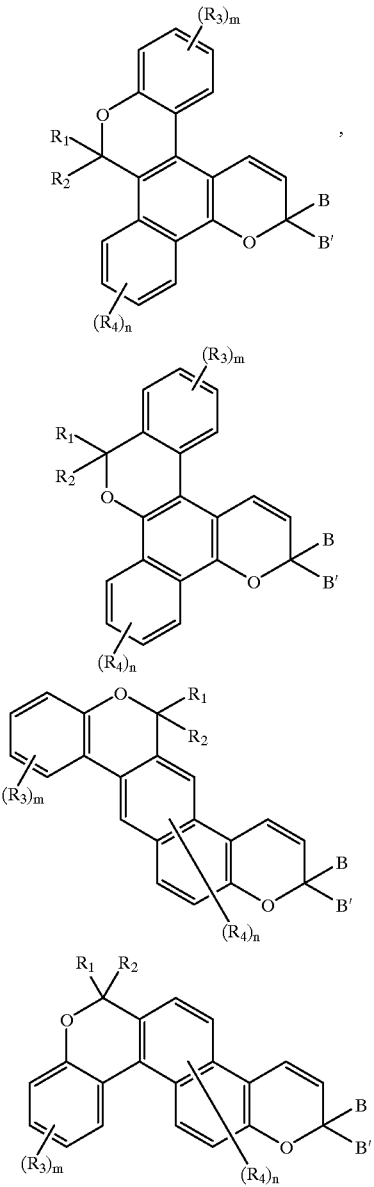

Also described are polymeric organic host materials that contain or that are coated with such compounds or combinations thereof with complementary photochromic compounds, e.g., certain other naphthopyrans, benzopyrans, and spiro(indoline)type compounds.

23 Claims, No Drawings

PHOTOCHROMIC BENZOPYRANO-FUSED NAPHTHOPYRANS

CROSS REFERENCE TO RELATED APPLICATIONS

This application is a continuation-in-part of application Ser. No. 09/114,089 filed Jul. 10, 1998 now U.S. Pat. No. 6,022,495.

DESCRIPTION OF THE INVENTION

The present invention relates to certain novel naphthopyran compounds. More particularly, this invention relates to novel photochromic benzopyrano-fused naphthopyran compounds. Still more particularly, this invention relates to compositions and articles containing such novel naphthopyran compounds. When exposed to electromagnetic radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in the '818 patent are the isomeric 2,2-diaryl-2H-naphtho[1,2-b]pyrans, which are reported to require unacceptably long periods of time to fade after activation.

U.S. Pat. No. 3,627,690 describes photochromic 2,2-di-substituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho[1,2-b]pyrans without the aforementioned additives ranges from several hours to many days to reach complete reversion.

U.S. Pat. No. 5,458,814 discloses photochromic 2H-naphtho[1,2-b]pyran compounds having certain substituents at the number 5 and 6 carbon atoms of the naphtho portion of the naphthopyran and at the 2-position of the pyran ring. These compounds have an acceptable fade rate in addition to a high activated intensity and a high coloration rate.

Although photochromic compounds are known, there is a need for new compounds that undergo a reversible color change at room temperature and demonstrate acceptable coloration rates and fade rates without the addition of acidic or basic components.

The present invention relates to novel substituted naphtho[1,2-b]pyran compounds having a substituted or unsubstituted benzopyrano group fused to the f side or face of the naphtho portion of the naphthopyran, which compounds may be represented by graphic formulae Ia and Ib hereinafter; and substituted naphtho[2,1-b]pyran compounds having a substituted or unsubstituted benzopyrano group fused to the i or h side of the naphtho portion of the naphthopyran, which compounds may be represented by graphic formulae Ic and Id hereinafter. All of these compounds also have certain substituents at the position ortho to the oxygen atom of the naphthopyran. These compounds have demonstrated an acceptable fade rate without the addition of acids or bases and an acceptable coloration rate—all as measured at room temperature.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-à-vis, glass lenses. Moreover, photochromic transparencies for vehicles, such as cars and airplanes, have been of interest because of the potential safety features that such transparencies offer.

In accordance with the present invention, it has now been discovered that certain novel dihydrobenzo(c)pyrano[4',3':3,4]naphtho[1,2-b]pyrans, dihydrobenzo(b)pyrano[4',3':3,4]naphtho[1,2-b]pyrans, dihydrobenzo(b)pyrano[4',3':6,7]naphtho[2,1-b]pyrans and dihydrobenzo(b)pyrano[4',3':5,6]naphtho[2,1-b]pyrans having activated colors ranging from red to purple, having acceptable properties, e.g., fade rate, activated intensity and coloration rate, may be prepared. These compounds may be described as the aforedescribed dihydrobenzopyrano-fused naphthopyrans having certain substituents at the position ortho to the oxygen atom of the naphthopyran ring. In particular, the compounds include 3,10-dihydrobenzo(c)pyrano[4',3':3,4]naphtho[1,2-b]pyrans and 3,9-dihydrobenzo(b)pyrano[4',3':3,4]naphtho[1,2-b]pyrans having certain substituents at the number 10 and 9 positions, respectively. Certain substituents may also be present at the number 5, 6, 7, 8, 11, 12, 13 or 14 carbon atoms of the compounds.

The invention further includes benzopyrano-fused[2,1-b]naphthopyrans having certain substituents at the position ortho to the oxygen atom of the naphthopyran ring. These compounds are 3,13-dihydrobenzo(b)pyrano[4',3':6,7]naphtho-[2,1-b]-pyrans having certain substituents at the number 13 position with certain other substituents optionally present at the number 5, 6, 7, 8, 9, 10, 11 and 14 positions. Also included in the invention are 2,7-dihydrobenzo(b)pyrano-[4',3':5,6]naphtho[2,1-b]pyrans having certain substituents at the number 7 position with certain other substituents optionally present at the number 5, 6, 9, 10, 11, 12, 13 and 14 positions.

These aforedescribed compounds may be represented by the following:

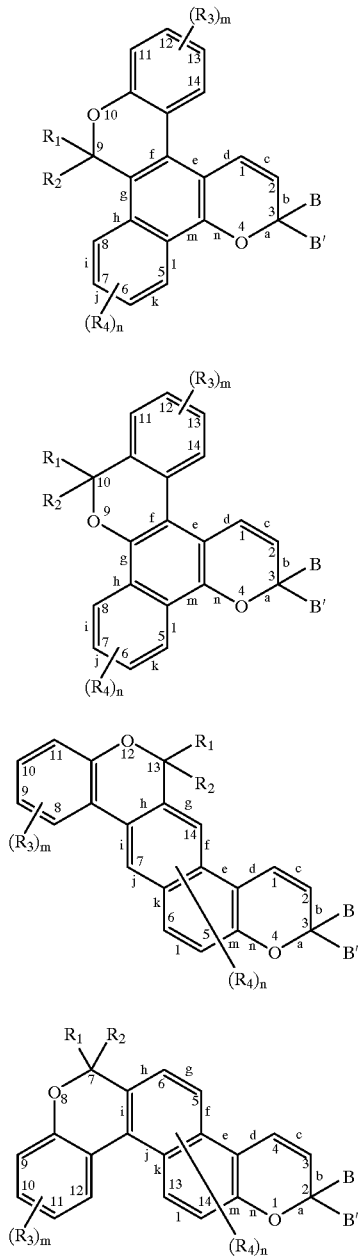

Ia

Ib

Ic

Id in which the letters a through n represent the sides or faces of the base naphthopyran structure, and the numbers 1 through 14 inside the rings identify the numbering sequence of the ring atoms of the benzopyrano-fused naphthopyran. In the definition of the substituents shown in graphic formulae Ia, Ib, Ic and Id, like symbols have the same meaning unless stated otherwise.

In graphic formulae Ia, Ib, Ic and Id, $R_1$ and $R_2$ may together form an oxo group, or $R_1$ and $R_2$ may each be hydrogen, $C_1$–$C_6$ alkyl, $C_3$–$C_7$ cycloalkyl, allyl, phenyl, mono- and di-substituted phenyl, benzyl or mono-substituted benzyl. Each of the phenyl and benzyl group substituents may be $C_1$–$C_6$ alkyl or $C_1$–$C_6$ alkoxy. Preferably, $R_1$ and $R_2$ are each selected from the group consisting of hydrogen, $C_1$–$C_4$ alkyl, $C_3$–$C_6$ cycloalkyl, phenyl, mono- or di-substituted phenyl, benzyl and mono-substituted benzyl. Each of the preferred phenyl and benzyl group substituents are $C_1$–$C_4$ alkyl or $C_1$–$C_4$ alkoxy. More preferably, $R_1$ and $R_2$ are each selected from the group consisting of hydrogen, $C_1$–$C_3$ alkyl, $C_3$–$C_5$ cycloalkyl, phenyl, mono- and di-substituted phenyl, benzyl and mono-substituted benzyl, each of such phenyl and benzyl group substituents being $C_1$–$C_3$ alkyl or $C_1$–$C_3$ alkoxy.

In graphic formulae Ia, Ib, Ic and Id, each $R_3$ and each $R_4$ may be selected from the group consisting of $C_1$–$C_6$ alkyl, $C_1$–$C_6$ alkoxy, chloro and fluoro, and m and n are each the integer 0, 1 or 2. Preferably, each $R_3$ and each $R_4$ are selected from the group consisting of $C_1$–$C_4$ alkyl, $C_1$–$C_4$ alkoxy and fluoro, and m and n are each the integer 0, 1, or 2. More preferably, $R_3$ and $R_4$ are each selected from the group consisting of $C_1$–$C_3$ alkyl and $C_1$–$C_3$ alkoxy and m and n are each the integer 0, 1 or 2.

B and B' in graphic formulae Ia, Ib, Ic and Id may each be selected from the group consisting of:

(i) the unsubstituted, mono-, di-, and tri-substituted aryl groups, phenyl and naphthyl;

(ii) the unsubstituted, mono- and di-substituted aromatic heterocyclic groups, pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, and fluorenyl, each of said aryl and aromatic heterocyclic substituents in parts (i) and (ii) being selected from the group consisting of hydroxy, aryl, mono($C_1$–$C_6$)alkoxyaryl, di($C_1$–$C_6$)alkoxyaryl, mono($C_1$–$C_6$)alkylaryl, di($C_1$–$C_6$)alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$) alkyl, $C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- and di-($C_1$–$C_6$)alkylaryl($C_1$–$C_6$)alkyl, mono- and di-($C_1$–$C_6$)alkoxyaryl($C_1$–$C_6$)alkyl, mono- and di-($C_1$–$C_6$)alkylaryl($C_1$–$C_6$)alkoxy, mono- and di-($C_1$–$C_6$)alkoxyaryl($C_1$–$C_6$)alkoxy, amino, mono($C_1$–$C_6$)alkylamino, di($C_1$–$C_6$)alkylamino, diarylamino, piperazino, N-($C_1$–$C_6$)alkylpiperazino, N-arylpiperazino, aziridino, indolino, piperidino, morpholino, thiomorpholino, tetrahydroquinolino, tetrahydroisoquinolino, pyrrolidyl, $C_1$–$C_6$ alkyl, $C_1$–$C_6$ chloroalkyl, $C_1$–$C_6$ fluoroalkyl, $C_1$–$C_6$ alkoxy, mono ($C_1$–$C_6$)alkoxy($C_1$–$C_4$)alkyl, acryloxy, methacryloxy, bromo, chloro and fluoro, said term aryl, as used in this part (ii) when referring to an aryl substituent, refers to phenyl or naphthyl;

(iii) the unsubstituted or mono-substituted groups, pyrazolyl, imidazolyl, indolyl, pyridyl, pyrazolinyl, imidazolinyl, pyrrolinyl, phenothiazinyl, phenoxazinyl, phenazinyl, or acridinyl, each of said substituents being selected from the group consisting of $C_1$–$C_6$ alkyl, $C_1$–$C_4$ alkoxy, phenyl, fluoro, chloro and bromo;

(iv) para-substituted phenyl wherein the para substituent is the linking group, —$(CH_2)_t$— or —O—$(CH_2)_t$—, wherein t is the integer 1, 2, 3, 4, 5 or 6, said linking group being connected to an aryl group, e.g. phenyl or naphthyl, which is a segment of another photochromic naphthopyran, such as naphtho[2,1-b]pyran or naphtho [1,2-b]pyran;

(v) the groups represented by the following graphic formulae:

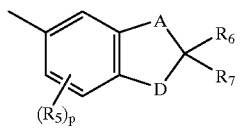

IIA

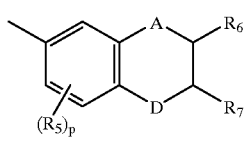

IIB wherein A is carbon or oxygen and D is oxygen or substituted nitrogen, provided that when D is substituted nitrogen, A is carbon, said nitrogen substituents being selected from the group consisting of hydrogen, $C_1$–$C_6$ alkyl, and $C_2$–$C_6$ acyl; each $R_5$ is $C_1$–$C_6$ alkyl, $C_1$–$C_6$ alkoxy, hydroxy, chloro or fluoro; $R_6$ and $R_7$ are each hydrogen or $C_1$–$C_6$ alkyl; and p is the integer 0, 1, or 2;

(vi) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$)alkoxy($C_3$–$C_6$)cycloalkyl, mono($C_1$–$C_6$)alkyl ($C_3$–$C_6$)-cycloalkyl, chloro($C_3$–$C_6$)cycloalkyl, fluoro ($C_3$–$C_6$)cycloalkyl and $C_4$–$C_{12}$ bicycloalkyl; and (vii) the group represented by the following graphic formula:

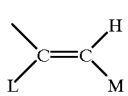

IIC wherein L in graphic formula IIC may be hydrogen or $C_1$–$C_4$ alkyl and M in graphic formula IIC may be selected from the unsubstituted, mono-, and di-substituted members of the group consisting of naphthyl, phenyl, furanyl, and thienyl, each of said group substituents in this part (vii) being $C_1$–$C_4$ alkyl, $C_1$–$C_4$ alkoxy, fluoro, or chloro.

Alternatively, B and B' taken together may form fluoren-9-ylidene, mono-, or di-substituted fluoren-9-ylidene or form a member selected from the group consisting of saturated $C_3$–$C_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene cycloundecylidene, and cyclododecylidene, saturated $C_7$–$C_{12}$ spiro-bicyclic hydrocarbon rings, e.g., bicyclo[2.2.1]heptylidene, i.e., norbornylidene, 1,7,7-trimethyl bicyclo[2.2.1]heptylidene, i.e., bornylidene, bicyclo[3.2.1]octylidene, bicyclo[3.3.1] nonan-9-ylidene, bicyclo[4.3.2]undecane, and saturated $C_7$–$C_{12}$ spiro-tricyclic hydrocarbon rings, e.g., tricyclo [2.2.1.0$^{2,6}$]heptylidene, tricyclo[3.3.1.1$^{3,7}$]decylidene, i.e., adamantylidene, and tricyclo[5.3.1.1$^{2,6}$]dodecylidene, each of said fluoren-9-ylidene substituents being selected from the group consisting of $C_1$–$C_4$ alkyl, $C_1$–$C_4$ alkoxy, fluoro and chloro.

Preferably, B and B' are each selected from the group consisting of: (i) phenyl, mono-substituted phenyl, and di-substituted phenyl, preferably substituted in the meta and/or para positions; (ii) the unsubstituted, mono- and di-substituted aromatic heterocyclic groups furanyl, benzofuran-2-yl, thienyl, benzothien-2-yl and dibenzofuranyl, each of said phenyl and aromatic heterocyclic substituents in parts (i) and (ii) being selected from the group consisting of hydroxy, phenyl($C_1$–$C_4$)alkyl, amino, mono($C_1$–$C_3$)alkylamino, di($C_1$–$C_3$)alkylamino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$) alkyl, fluoro and chloro; (iii) the groups represented by the graphic formulae IIA and IIB, wherein A is carbon and D is oxygen, $R_5$ is $C_1$–$C_3$ alkyl or $C_1$–$C_3$ alkoxy, $R_6$ and $R_7$ are each hydrogen or $C_1$–$C_3$ alkyl; and p is the integer 0 or 1; (iv) $C_1$–$C_4$ alkyl; and (v) the group represented by the graphic formula IIC wherein L is hydrogen or methyl and M is phenyl or mono-substituted phenyl, said phenyl substituent being selected from the group consisting of $C_1$–$C_3$ alkyl, $C_1$–$C_3$ alkoxy, and fluoro; or (vi) B and B' taken together form fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, said fluoren-9-ylidene substituent being selected from the group consisting of $C_1$–$C_3$ alkyl, $C_1$–$C_3$ alkoxy, fluoro and chloro.

More preferably, B and B' are each selected from the group consisting of (i) phenyl, mono- and di-substituted phenyl, (ii) the unsubstituted, mono- and di-substituted aromatic heterocyclic groups furanyl, benzofuran-2-yl, thienyl, benzothien-2-yl and dibenzofuranyl, each of said phenyl and aromatic heterocyclic substituents being selected from the group consisting of hydroxy, phenyl($C_1$–$C_3$)alkyl, $C_1$–$C_3$ alkyl, $C_1$–$C_3$ alkoxy, fluoro and chloro; and (iii) the group represented by graphic formula IIA, wherein A is carbon and D is oxygen, $R_5$ is $C_1$–$C_3$ alkyl or $C_1$–$C_3$ alkoxy, $R_6$ and $R_7$ are each hydrogen or $C_1$–$C_3$ alkyl, and p is the integer 0 or 1; or (iv) B and B' taken together form fluoren-9-ylidene, adamantylidene, bornylidene, norbornylidene, or bicyclo[3.3.1]nonan-9-ylidene.

Compounds represented by graphic formula Ia may be prepared by the following steps. Benzophenones represented by graphic formula V and VA in Reactions A and B, respectively, are either purchased or prepared by Friedel-Crafts methods using an appropriately substituted or unsubstituted benzoyl chloride of graphic formula IV and a commercially available substituted or unsubstituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

The compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (or VA in Reaction B). R and R' represent potential phenyl substituents, as described hereinbefore.

REACTION A

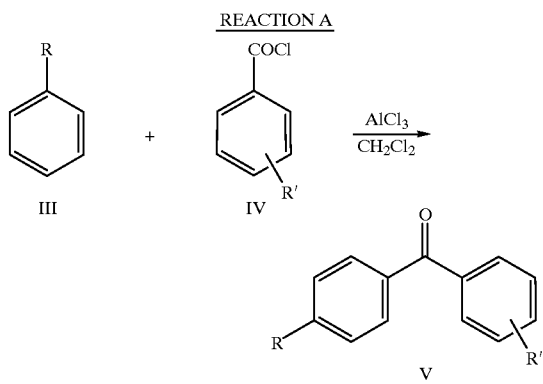

In Reaction B, the substituted or unsubstituted ketone represented by graphic formula VA, in which B and B' may represent groups other than substituted or unsubstituted phenyl, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or for example, from ketones prepared via reaction of an acyl halide with a substituted or unsubstituted benzene, naphthalene, or heteroaromatic compound. Propargyl alcohols having B or B' groups represented by graphic formula IIC may be prepared by the methods described in U.S. Pat. No. 5,274,132, column 2, lines 40 to 68.

REACTION B

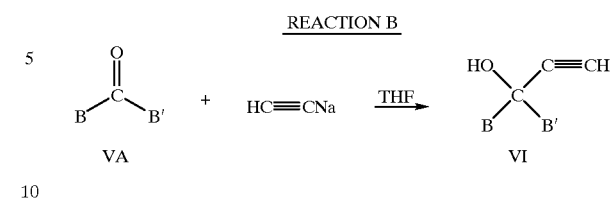

Naphthopyrans represented by graphic formula XI, which are used in the preparation of naphthopyrans of graphic formula Ia, may be prepared as described in Reaction C. In Reaction C, a substituted 2-bromoacetophenone represented by graphical formula VII is reacted with dimethyl malonate represented by graphic formula VIII in the presence of copper (I) bromide and sodium hydride to produce methyl-1,3-dihydroxy-4-naphthoate represented by IX. See Bruggink, A. and McKillop, A., *Tetrahedron*, Vol. 31, pp 2607–2619, 1975.

In the next step, the naphthol represented by graphic formula IX is coupled with the propargyl alcohol represented by VI in the presence of a catalytic amount of an acid, e.g., p-toluenesulfonic acid (p-TSA), in a suitable solvent such as chloroform to produce the naphthopyran represented by graphic formula X. Compound X is reacted with methyl iodide in the presence of a base, e.g., potassium carbonate, in a suitable solvent such as acetone to produce naphthopyran represented by graphic formula XI.

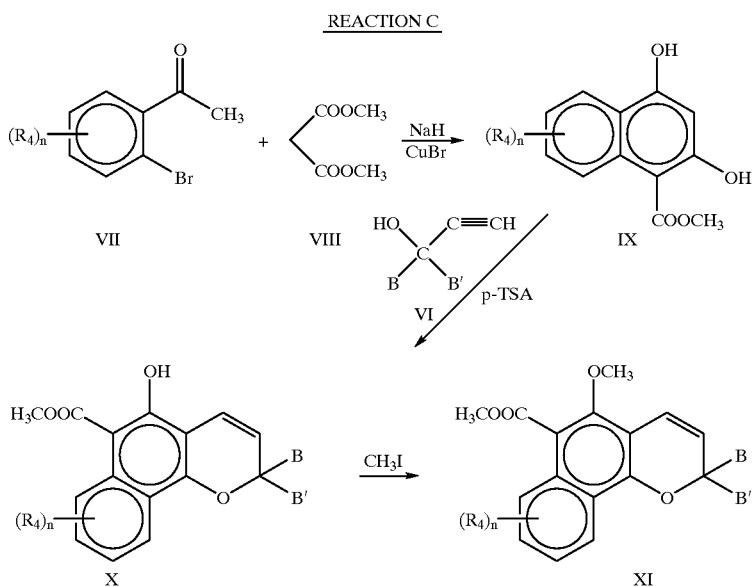

In Reaction D, o-bromophenol represented by graphic formula XII is reacted with tetrahydropyran (THP) represented by graphic formula XIII in the presence of a catalytic amount of pyridinium para-toluene sulfonate (PPTS) in a suitable solvent such as methylene chloride to produce the THP-protected bromophenol represented by graphic formula XIV. Compound XIV is reacted with magnesium turnings in a suitable solvent such as tetrahydrofuran (THF) in the presence of an initiator, e.g., dibromoethane, yielding the THP-protected ortho-phenol magnesium bromide represented by graphic formula XV.

REACTION D

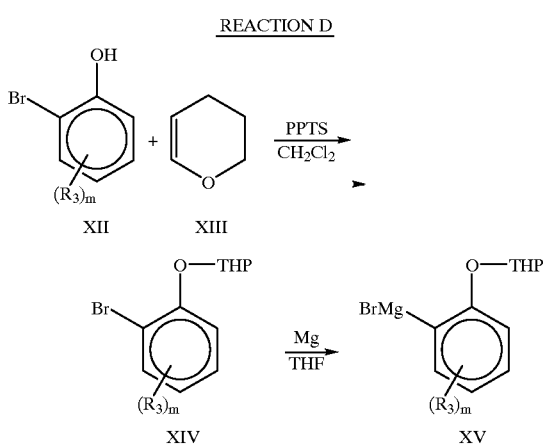

In Reaction E, compound XV is reacted with the naphthopyran represented by graphic formula XI (produced in Reaction C) in a suitable solvent such as tetrahydrofuran, to produce the desired benzopyrano-fused naphthopyrans represented by graphic formula XVI. The naphthopyrans represented by graphic formula XVI are recovered from the reaction mixture by separation methods known in the art.

REACTION E

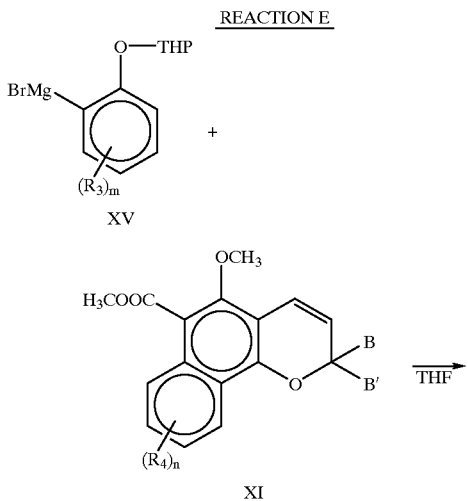

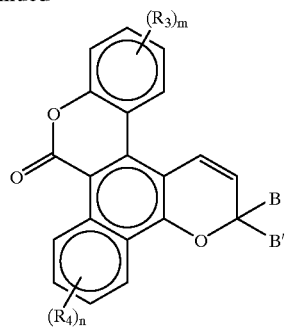

Naphthopyrans represented by graphic formula XXI in Reaction H, which are used in preparation of naphthopyran of graphic formula Ib, may be prepared as described in reaction F, G, and H. In reaction F, a substituted methyl-2-aminobenzoate represented by graphical formula XVII is first reacted with sodium nitrite under acidic conditions, e.g., hydrochloric acid, followed by reaction with sodium tetrafluoroborate to produce an intermediate. The resulting intermediate mixture is reacted with a substituted naphthoquinone represented by graphic formula XVIII in the presence of copper under acidic conditions, e.g., acetic acid (AA). A mixture of naphthoquinones is produced. The desired product is represented by graphic formula XIX.

REACTION F

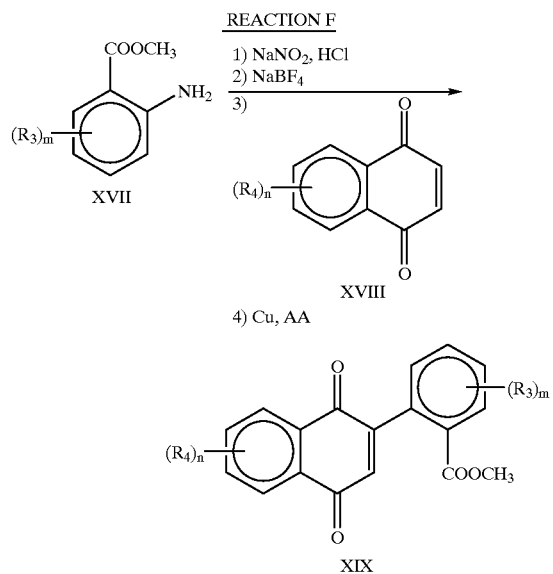

In Reaction G, the naphthoquinone mixture which contains the naphthoquinone represented by graphic formula XIX is reduced with a mixture of zinc and acetic acid to produce the desired naphthol represented by the graphic formula XX. The desired naphthol was recovered or separated from the naphthol mixture by known separation methods, e.g., chromatography, extraction, crystallization, etc.

REACTION G

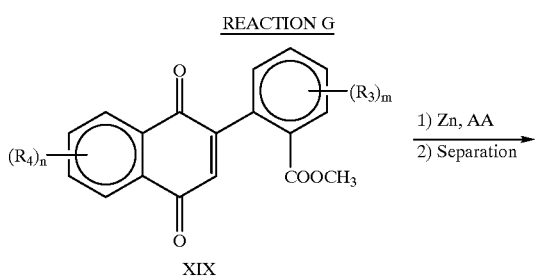

In Reaction H, the naphthol represented by graphic formula XX is coupled with the propargyl alcohol represented by VI in the presence of a catalytic amount of an acid, e.g., p-toluenesulfonic acid, in a suitable solvent such as chloroform to produce the naphthopyran represented by graphic formula XXI.

REACTION H

In Reaction I, the compounds represented by graphic formula XXI may be reduced, for example, with lithium aluminum hydride (LAH) in an inert solvent such as tetrahydrofuran (THF) to give compounds represented by graphic formula XXII. Alternatively, the oxo group of compound XXI may be reacted with a Grignard reagent (R"MgX in which R" represents substituents $R_1$ and $R_2$) to produce the substituted benzopyrano-fused naphthopyran of graphic formula XXIII.

REACTION I

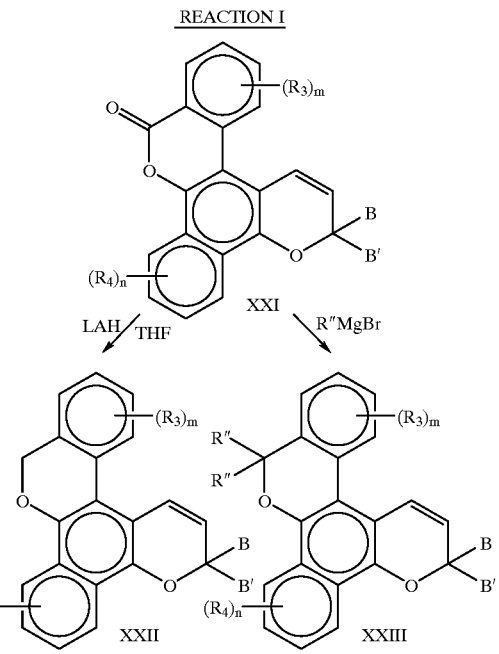

Reaction J describes a method of preparing a naphthopyran of the type represented by graphic formula Id. The naphthol represented by graphic formula XXIV, which is prepared according to the methods disclosed in U.S. Pat. No. 3,829,443, the disclosure of which is incorporated herein by reference, is coupled with the propargyl alcohol represented by graphic formula VI in the presence of a catalytic amount of an acid (pTSA), in a suitable solvent such as chloroform to produce the naphthopyran represented by graphic formula XXV. Compound XXV is reacted with methyl iodide in presence of a base, e.g., potassium carbonate, in a suitable solvent such as acetone to produce the naphthopyran of graphic formula XXVI. In next step, the THP protected ortho-phenol magnesium bromide represented by graphic formula XV is reacted with naphthopyran represented by the graphic formula XXVI to produce the naphthopyran represented by graphic formula XXVII.

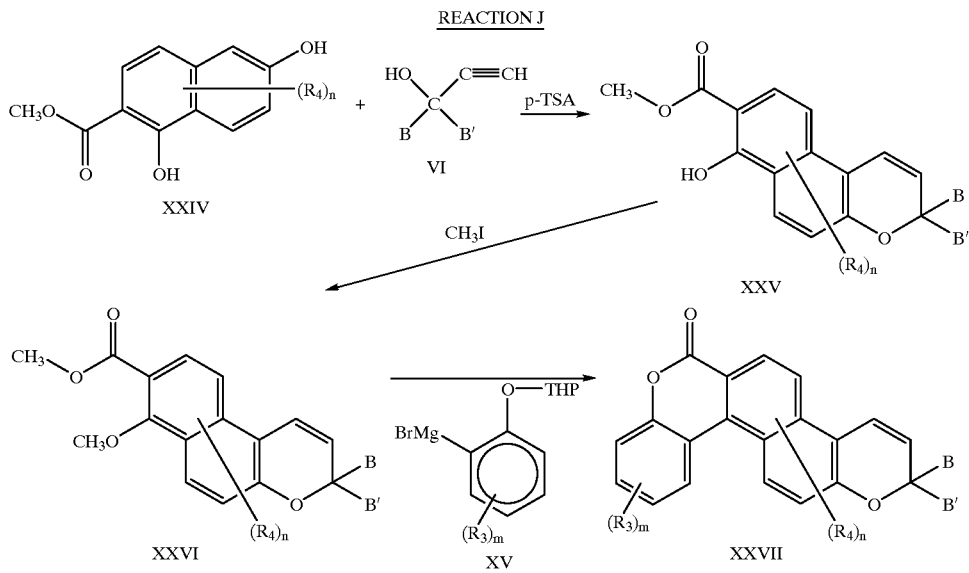

REACTION J

Reaction K describes a method of preparing a naphthopyran of the type represented by graphic formula Ic. The THP protected ortho-phenol magnesium bromide represented by graphic formula XV is reacted with the naphthopyran represented by graphic formula XXVIII, the preparation of which is disclosed in U.S. Pat. No. 5,466,398, to produce the naphthopyran represented by graphic formula XXIX.

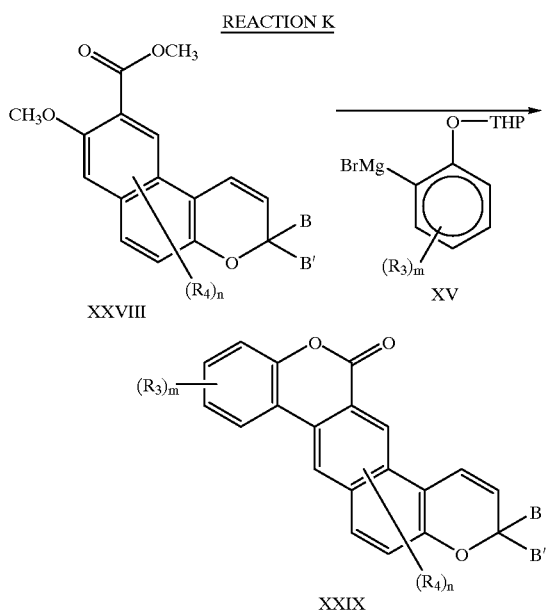

REACTION K

Compounds represented by graphic formulae Ia, Ib, Ic and Id may be used in those applications in which organic photochromic substances may be employed, such as optical lenses, e.g., vision correcting ophthalmic lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. The benzopyrano-fused naphthopyrans represented by graphic formulae Ia and Ib exhibit color changes from colorless to colors ranging from yellow to blue. The benzopyrano-fused naphthopyrans represented by graphic formulae Ic and Id exhibit color changes from colorless to colors ranging from yellow to purple.

Examples of contemplated naphthopyran compounds within the scope of the invention include the following:

(a) 3,3-bis(4-methoxyphenyl)-13-oxo-3,13-dihydrobenzo(b)pyrano-[4',3':6,7]naphtho(2,1-b)pyran;

(b) 2-phenyl-2-(4-methoxyphenyl)-7-oxo-2,7-dihydrobenzo(b)pyrano[4',3':5,6]naphtho(2,1-b)pyran;

(c) 2,2-diphenyl-7-oxo-2,7-dihydrobenzo(b)pyrano[4',3':5,6]naphtho(2,1-b)pyran;

(d) 3,3-diphenyl-10-oxo-3,10-dihydrobenzo(c)pyrano-[4',3':3,4]naphtho(1,2-b)pyran;

(e) 3,3-bis(4-methoxyphenyl)-10-oxo-3,10-dihydrobenzo(c)pyrano[4',3':3,4]naphtho(1,2-b)pyran;

(f) 3,3-bis(4-methoxyphenyl)-10,10-dimethyl-3,10-dihydrobenzo(c)pyrano[4',3':3,4]naphtho(1,2-b)pyran;

(g) 3-(4-methoxyphenyl)-3-(4-morpholinophenyl)-10-oxo-3,10-dihydrobenzo(c)pyrano[4',3':3,4]naphtho(1,2-b)pyran;

(h) 3,3-diphenyl-9-oxo-3,9-dihydrobenzo(b)pyrano[4',3':3,4]naphtho(1,2-b)pyran; and (i) 3-(4-methoxyphenyl)-3-phenyl-9-oxo-3,9-dihydrobenzo(b)pyrano[4',3':3,4]naphtho(1,2-b)pyran.

It is contemplated that the organic photochromic naphthopyrans of the present invention may be used alone, in combination with other naphthopyrans of the present invention, or in combination with one or more other appropriate complementary organic photochromic materials, i.e., organic photochromic compounds having at least one activated absorption maxima within the range of between about 400 and 700 nanometers, or substances containing same, and may be incorporated, e.g., dissolved or dispersed, in or applied to (in an appropriate carrier, such as a solvent or organic polymer) a polymeric organic host material used to prepare photochromic articles and which color when activated to an appropriate hue.

Other than where otherwise indicated, all values such as those expressing wavelengths, quantities of ingredients or reaction conditions, used herein are to be understood as modified in all instances by the term "about".

Examples of complementary organic photochromic compounds include other naphthopyrans, chromenes, oxazines, substituted 2H-phenanthro[4,3-b]pyran and 3H-phenanthro[1,2-b]pyran compounds, benzopyran compounds having substituents at the 2-position of the pyran ring including a dibenzo-fused 5 member heterocyclic compound and a substituted or unsubstituted heterocyclic ring, such as a benzothieno or benzofurano ring fused to the benzene portion of the benzopyrans, indenonaphthopyrans, spiro(benzindoline)naphthopyrans, spiro(indoline)benzopyrans, spiro(indoline)naphthopyrans, spiro(indoline)quinopyrans, spiro(indoline)pyrans, spiro(indoline)naphthoxazines, spiro(indoline)pyridobenzoxazines, spiro(benzindoline)pyridobenzoxazines, spiro(benzindoline)naphthoxazines, spiro(indoline)benzoxazines, and mixtures of such photochromic compounds. Many of such photochromic compounds are described in the open literature, e.g., U.S. Pat. Nos. 3,562,172; 3,567,605; 3,578,602; 4,215,010; 4,342,668; 4,816,584; 4,818,096; 4,826,977; 4,880,667; 4,931,219; 5,066,818; 5,238,931; 5,274,132; 5,384,077; 5,405,958; 5,429,774; 5,458,814; 5,466,398; 5,514,817; 5,552,090; 5,552,091; 5,565,147; 5,573,712; 5,578,252; 5,637,262; 5,645,767; 5,656,206; 5,658,500; 5,658,501; 5,674,432, 5,698,141, 5,723,072, 5,744,070, 5,783,116 and 5,811,034. Spiro(indoline)pyrans are also described in the text, *Techniques in Chemistry*, Volume III, "Photochromism", Chapter 3, Glenn H. Brown, Editor, John Wiley and Sons, Inc., New York, 1971.

The complementary organic photochromic materials may also include polymerizable photochromic compounds, such as those disclosed in U.S. Pat. Nos. 4,719,296; 5,166,345; 5,236,958; 5,252,742; 5,359,035; and 5,488,119.

Other complementary photochromic substances contemplated are photochromic metal-dithizonates, e.g. mercury dithizonates which are described in, for example, U.S. Pat. No. 3,361,706, and fulgides and fulgimides, e.g. the 3-furyl and 3-thienyl fulgides and fulgimides which are described in U.S. Pat. No. 4,931,220 at column 20, line 5 through column 21, line 38.

The disclosures relating to such photochromic compounds in the aforedescribed patents are incorporated herein, in toto, by reference. The photochromic articles of the present invention may contain one photochromic compound or a mixture of photochromic compounds, as desired.

Each of the photochromic substances described herein may be used in amounts (or in a ratio) such that an organic host material or substrate to which the photochromic compounds or mixture of compounds is associated, exhibits a desired resultant color, e.g., a substantially neutral color when activated with unfiltered sunlight, i.e., as near a neutral color as possible given the colors of the activated photochromic compounds. Neutral gray and neutral brown colors are preferred. Further discussion of neutral colors and ways to describe colors may be found in U.S. Pat. No. 5,645,767 column 12, line 66 to column 13, line 19.

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from 0.05 to 2.0, e.g., from 0.2 to 1.0, milligrams per square centimeter of surface to which the photochromic substance (s) is incorporated or applied. The amount of photochromic material incorporated into a coating composition may range from 0.1 to 40 weight percent, based on the weight of the liquid coating composition.

The photochromic naphthopyrans of the present invention may be associated with the host material by various methods described in the art. See, for example, column 13, lines 40 to 58 of U.S. Pat. No. 5,645,767. Aqueous or organic solutions of the photochromic compounds may be used to incorporate the photochromic compounds into a polymeric organic host material or other materials such as textiles and polymeric coating compositions. Polymeric coating compositions may be applied to the substrate using a coating process such as that described in U.S. Pat. No. 3,971,872, the disclosure of which is incorporated herein by reference.

Application of the polymeric coating may be by any of the methods used in coating technology such as, for example, spray coating, spin coating, spread coating, curtain coating, dip coating, casting or roll-coating and methods used in preparing overlays, such as the method of the type described in U.S. Pat. No. 4,873,029, which is incorporated herein by reference. The application method selected also depends on the thickness of the cured coating. Coatings having a thickness ranging from 1 to 50 microns may be applied by conventional methods used in coating technology. Coatings of a thickness greater than 50 microns may require molding methods typically used for overlays.

The host material will usually be transparent, but may be translucent or even opaque. The host material need only be pervious to that portion of the electromagnetic spectrum, which activates the photochromic substance, i.e., that wavelength of ultraviolet (UV) light that produces the open or colored form of the substance and that portion of the visible spectrum that includes the absorption maximum wavelength of the substance in its UV activated form, i.e., the open form. Preferably, the host color should not be such that it masks the color of the activated form of the photochromic compounds, i.e., so the change in color is readily apparent to the observer. Compatible tints may be applied to the host material as described in U.S. Pat. No. 5,645,767 in column 13, line 59 to column 14, line 3.

Most preferably, the polymeric organic host material is a solid transparent or optically clear material, e.g., materials suitable for optical applications, such as plano, ophthalmic and contact lenses, windows, automotive transparencies, e.g., windshields, aircraft transparencies, plastic sheeting, polymeric films, etc.

Examples of polymeric organic host materials which may be used with the photochromic compounds described herein include: polymers, i.e., homopolymers and copolymers, of the bis(allyl carbonate) monomers, diethylene glycol dimethacrylate monomers diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers, alkoxylated polyhydric alcohol acrylate monomers, such as ethoxylated trimethylol propane triacrylate monomers, urethane acrylate monomers, such as those described in U.S. Pat. No. 5,373,033, and vinylbenzene monomers, such as those described in U.S. Pat. No. 5,475,074 and styrene; polymers, i.e., homopolymers and copolymers, of mono- or polyfunctional, e.g., di- or multi-functional, acrylate and/or methacrylate monomers, poly($C_1$–$C_{12}$ alkyl methacrylates), such as poly(methyl methacrylate), poly(oxyalkylene)dimethacrylate, poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polythiourethanes, thermoplastic polycarbonates, polyesters, poly(ethylene terephthalate), polystyrene, poly (alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Further examples of polymeric organic host materials are disclosed in the U.S. Pat. No. 5,753,146, column 8, line 62 to column 10, line 34, which disclosure is incorporated herein by reference.

Transparent copolymers and blends of transparent polymers are also suitable as host materials. Preferably, the host material or substrate for the photochromic polymeric coating composition is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polythiourethanes, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly, contemplated is use of the photochromic naphthopyrans of the present invention with optical organic resin monomers used to produce optically clear coatings and polymerizates, i.e., materials suitable for optical applications, such as for example lenses, i.e., plano, ophthalmic and contact lenses. Optically clear polymerizates may have a refractive index that may range from about 1.48 to about 1.75, e.g., from about 1.495 to about 1.66.

Specifically contemplated are polymerizates of optical resins sold by PPG Industries, Inc. under the CR-designation, e.g., CR-307 and CR-407, and polymerizates prepared for use as hard or soft contact lenses. Methods for producing both types of contact lenses are disclosed in U.S. Pat. No. 5,166,345, column 11, line 52, to column 12, line 52, which disclosure is incorporated herein by reference. Additional polymerizates contemplated for use with the photochromic naphthopyrans of the present invention are polymerizates used to form soft contact lenses with high moisture content described in U.S. Pat. No. 5,965,630 and extended wear contact lenses described in U.S. Pat. No. 5,965,631, both disclosures of which are incorporated herein by reference.

The present invention is more particularly described in the following examples which are intended as illustrative only, since numerous modifications and variations therein will be apparent to those skilled in the art.

EXAMPLE 1

Step 1

Methyl 2-aminobenzoate (10 grams) was added to a reaction flask containing 20 milliliters (mL) of concentrated hydrochloric acid and mixed. The reaction mixture was cooled to 0° C. Sodium nitrate (5 weight percent aqueous solution) was added dropwise in excess, with stirring. An aqueous suspension of sodium tetrafluoroborate was added dropwise to the reaction mixture and the reaction mixture was stirred for an additional 0.5 hour.

Step 2

The solution from Step 1 was added dropwise, with stirring, to a reaction flask containing a suspension of naphthoquinone (10 grams) in 120 milliliters (mL) of acetic acid. Copper powder (4 grams) was added to the reaction mixture over the course of 6 hours. Solvent was evaporated leaving a residue which was partially dissolved in toluene and the solids were separated by filtration. The organic filtrate was concentrated to yield 20 grams of a mixture consisting of 1,4-naphthoquinone, 2,3-bis(2-methoxycarbonylphenyl)-1,4-naphthoquinone and the desired product 2-(2-methoxycarbonyl-phenyl)-1,4-naphthoquinone.

Step 3

The product mixture from Step 2 (10 grams) was added to a reaction flask containing 50 milliliters (mL) of acetic acid and stirred at ambient temperature. Zinc dust (3 grams) was added incrementally, and the reaction mixture was allowed to stir for 5 hours at ambient temperature. The reaction mixture was filtered, the filtrate was mixed with water and extracted with a 1:1 mixture of ethyl ether/tetrahydrofuran. The organic phase was concentrated to yield 2.5 gram of a solid, which was washed with ether and dried in air. An NMR spectrum showed the product to have a structure consistent with 12-hydroxy-6H-dibenzo[c,h]chromen-6-one.

Step 4

12-Hydroxy-6H-dibenzo[c,h]chromen-6-one (1 gram) from Step 3 and 2,2-diphenyl-2-propyn-1-ol (1.5 gram) were mixed into a reaction flask containing chloroform (50 mL) and stirred at room temperature. p-Toluenesulfonic acid (0.1 gram) was added to the reaction mixture which was stirred for 6 hours. The reaction mixture was concentrated and the residue was purified by column chromatography using a chloroform-hexane mixture (1:1 by volume) as the eluant. The fractions containing the desired product were collected, combined and concentrated; the resulting residue was recrystallized from ethyl ether to yield 1.0 gram of crystals having a melting point of 252–254° C. An NMR spectrum showed the product to have a structure consistent with 3,3-diphenyl-10-oxo-3,10-dihydrobenzo(c)pyrano[4',3':3,4] naphtho(1,2-b)pyran.

EXAMPLE 2

Part A

Testing was done with the photochromic compound prepared in Example 1 in the following manner. A quantity of the photochromic compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic compound was dissolved into the monomer blend by stirring and gentle heating. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours, lower it to 60° C. over a 2 hour interval and then hold at 60° C. for 16 hours. After the mold was opened, the polymer sheet was cut using a diamond blade saw into 2 inch (5.1 centimeters) test squares.

Part B

The photochromic test square prepared in Part A were tested for photochromic response on an optical bench. Prior to testing on the optical bench, the photochromic test square was exposed to 365 nanometer ultraviolet light for about 15 minutes to activate the photochromic compounds and then placed in a 76° C. oven for about 15 minutes to bleach or inactivate the photochromic compounds. The test square was then cooled to room temperature, exposed to fluorescent room lighting for at least 2 hours and then kept covered for at least 2 hours prior to testing on an optical bench maintained at 72° F. (22.2° C.). The bench was fitted with a 300 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. The power output of the optical bench, i.e., the dosage of light that the sample lens would be exposed to, was calibrated with a photochromic test square used as a reference standard. This resulted in a power output ranging from 0.10 to 0.13 milliwatts per square centimeter ($mW/cm^2$). Measurement of the power output was made using a GRASEBY Optronics Model S-371 portable photometer (Serial #21536) with a UV-A detector (Serial #22411) or comparable equipment. The UV-A detector was placed into the sample holder and the light output was measured. Adjustments to the power output were made by increasing or decreasing the lamp wattage or by adding or removing neutral density filters in the light path.

A monitoring, collimated beam of light from a tungsten lamp was passed through the square at a small angle (approximately 30°) normal to the square. After passing through the square, the light from the tungsten lamp was directed to a detector through Spectral Energy Corp. GM-200 monochromator set at the previously determined visible lambda max of the photochromic compound being measured. The output signals from the detector were processed by a radiometer.

Change in optical density ($\Delta OD$) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula: $\Delta OD = \log(100/\%Ta)$, where % Ta is the percent transmittance in the activated state and the logarithm is to the base 10.

The optical properties of the photochromic compound in the test square are reported in Table 1. The $\Delta$ OD/min, which represents the sensitivity of the photochromic compound's response to UV light, was measured over the first five (5) seconds of UV exposure, then expressed on a per minute basis. The saturation optical density ($\Delta$ OD@ Saturation) was taken under identical conditions as the $\Delta$ OD/min, except UV exposure was continued for 15 minutes. The lambda max (Vis) is the wavelength in nanometers (nm) in the visible spectrum at which the maximum absorption of the activated (colored) form of the photochromic compound in a test square occurs. The lambda max (Vis) wavelength was determined by testing the photochromic test square polymerizate of Part A in a Varian Cary 3 UV-Visible spectrophotometer. The Bleach Rate (T ½) is the time interval in seconds for the absorbance of the activated form of the photochromic compound in the test square to reach one half the highest absorbance at room temperature (72° F., 22.2° C.) after removal of the source of activating light.

TABLE 1

| Compound Example | lambda max (Vis) nanometers | Sensitivity $\Delta OD/min$ | $\Delta OD$ @ Saturation | Bleach Rate T ½ (sec) |
| --- | --- | --- | --- | --- |
| 1 | 481 | 0.19 | 0.15 | 45 |

The results of Table 1 show that the test square prepared using the Compound of Example 1 demonstrated a lambda max (visible) of 481 nm, a coloration rate (sensitivity) of 0.19, an activated intensity ($\Delta OD$ at Saturation) of 0.15, and a fade or bleach rate of 45 seconds.

The present invention has been described with reference to specific details of particular embodiments thereof. It is not intended that such details be regarded as limitations upon the scope of the invention except insofar as to the extent that they are included in the accompanying claims.

I claim:
1. A naphthopyran compound represented by the following:

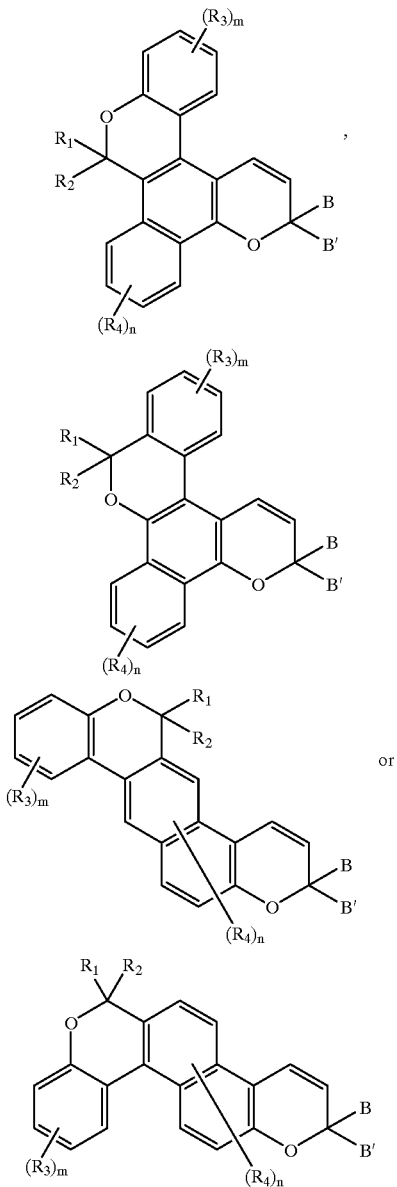

wherein,
(a) $R_1$ and $R_2$ together form an oxo group or $R_1$ and $R_2$ are each hydrogen, $C_1$–$C_6$ alkyl, $C_3$–$C_7$ cycloalkyl, allyl, phenyl, mono- or di-substituted phenyl, benzyl or mono-substituted benzyl, each of said phenyl and benzyl group substituents being $C_1$–$C_6$ alkyl or $C_1$–$C_6$ alkoxy;
(b) each $R_3$ and $R_4$ are selected from the group consisting of $C_1$–$C_6$ alkyl, $C_1$–$C_6$ alkoxy, chloro and fluoro, and m and n are each the integer 0, 1 or 2; and
(c) B and B' are each selected from the group consisting of:
  (i) the unsubstituted, mono-, di-, and tri-substituted aryl groups, phenyl and naphthyl;
  (ii) the unsubstituted, mono- and di-substituted heteroaromatic groups, pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, and fluorenyl, each of said aryl and heteroaromatic substituents in (d) (i) and (ii) being selected from the group consisting of hydroxy, aryl, mono($C_1$–$C_6$)alkoxyaryl, di($C_1$–$C_6$)alkoxyaryl, mono($C_1$–$C_6$)alkylaryl, di($C_1$–$C_6$)alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- and di-($C_1$–$C_6$)alkylaryl ($C_1$–$C_6$)alkyl, mono- and di-($C_1$–$C_6$)alkoxyaryl ($C_1$–$C_6$)alkyl, mono- and di-($C_1$–$C_6$)alkylaryl ($C_1$–$C_6$)alkoxy, mono- and di-($C_1$–$C_6$)alkoxyaryl ($C_1$–$C_6$)alkoxy, amino, mono($C_1$–$C_6$)alkylamino, di($C_1$–$C_6$)alkylamino, diarylamino, piperazino, N-($C_1$–$C_6$)alkylpiperazino, N-arylpiperazino, aziridino, indolino, piperidino, morpholino, thiomorpholino, tetrahydroquinolino, tetrahydroisoquinolino, pyrrolidyl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro and fluoro, said aryl group being phenyl or naphthyl;
  (iii) the unsubstituted or mono-substituted groups diarylamino, pyrazolyl, imidazolyl, indolyl, pyridyl, pyrazolinyl, imidazolinyl, pyrrolinyl, phenothiazinyl, phenoxazinyl, phenazinyl, or acridinyl, said aryl group being phenyl or naphthyl, each of said substituents being selected from the group consisting of $C_1$–$C_6$ alkyl, $C_1$–$C_4$ alkoxy, phenyl, fluoro, chloro and bromo;
  (iv) para-substituted phenyl wherein said para substituent is the linking group, —$(CH_2)_t$— or —O—$(CH_2)_t$—, wherein t is the integer 1, 2, 3, 4, 5 or 6, said linking group being connected to an aryl group, which is a segment of another photochromic naphthopyran;
  (v) the groups represented by the following graphic formulae:

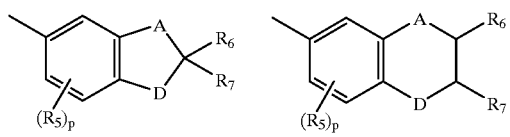

wherein A is carbon or oxygen and D is oxygen or substituted nitrogen, provided that when D is substituted nitrogen, A is carbon, said nitrogen substituents being selected from the group consisting of hydrogen, $C_1$–$C_6$ alkyl, and $C_2$–$C_6$ acyl; each $R_5$ is $C_1$–$C_6$ alkyl, $C_1$–$C_6$ alkoxy, hydroxy, chloro or fluoro; $R_6$ and $R_7$ are each hydrogen or $C_1$–$C_6$ alkyl; and p is the integer 0, 1, or 2;
  (vi) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$) alkoxy($C_3$–$C_6$)cycloalkyl, mono($C_1$–$C_6$)alkyl($C_3$–$C_6$)cycloalkyl, chloro ($C_3$–$C_6$)cycloalkyl, fluoro($C_3$–$C_6$)cycloalkyl and $C_4$–$C_{12}$ bicycloalkyl; and
  (vii) the group represented by the following graphic formula:

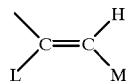

wherein L is hydrogen or $C_1$–$C_4$ alkyl and M is selected from the unsubstituted, mono-, and di-substituted members of the group consisting of naphthyl, phenyl, furanyl, and thienyl, each of said group substituents being $C_1$–$C_4$ alkyl, $C_1$–$C_4$ alkoxy, fluoro, or chloro; or (e) B and B' taken together form fluoren-9-ylidene, mono-, or di-substituted fluoren-9-ylidene or a member selected from the group consisting of saturated $C_3$–$C_{12}$ spiro-monocyclic hydrocarbon rings, saturated $C_7$–$C_{12}$ spiro-bicyclic hydrocarbon rings, and saturated $C_7$–$C_{12}$ spiro-tricyclic hydrocarbon rings, each of said fluoren-9-ylidene substituents being selected from the group consisting of $C_1$–$C_4$ alkyl, $C_1$–$C_4$ alkoxy, fluoro and chloro.

2. The naphthopyran of claim 1 wherein, (a) $R_1$ and $R_2$ are each hydrogen, $C_1$–$C_4$ alkyl, $C_3$–$C_6$ cycloalkyl, phenyl, mono- or di-substituted phenyl, benzyl or mono-substituted benzyl, each of said phenyl and benzyl group substituents being $C_1$–$C_4$ alkyl or $C_1$–$C_4$ alkoxy;

(b) each $R_3$ and $R_4$ are selected from the group consisting of $C_1$–$C_4$ alkyl, $C_1$–$C_4$ alkoxy and fluoro, and m and n are each the integer 0, 1, or 2; and (c) B and B' are each selected from the group consisting of:

(i) phenyl, mono-substituted phenyl, and di-substituted phenyl;

(ii) the unsubstituted, mono-, and di-substituted aromatic heterocyclic groups furanyl, benzofuran-2-yl, thienyl, benzothien-2-yl and dibenzofuranyl, said phenyl and aromatic heterocyclic substituents in (d)(i) and (ii) being selected from the group consisting of hydroxy, phenyl($C_1$–$C_4$)alkyl, amino, mono($C_1$–$C_3$)alkylamino, di($C_1$–$C_3$)alkylamino, piperidino, morpholino, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, fluoro and chloro;

(iii) the groups represented by the following graphic formulae:

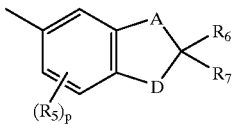 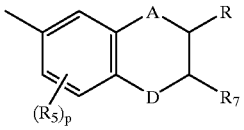

wherein A is carbon and D is oxygen, $R_5$ is $C_1$–$C_3$ alkyl or $C_1$–$C_3$ alkoxy, $R_6$ and $R_7$ are each hydrogen or $C_1$–$C_3$ alkyl; and p is the integer 0 or 1;

(iv) $C_1$–$C_4$ alkyl; and (v) the group represented by the following graphic formula:

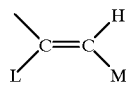

wherein L is hydrogen or methyl and M is phenyl or mono-substituted phenyl, said phenyl substituent being selected from the group consisting of $C_1$–$C_3$ alkyl, $C_1$–$C_3$ alkoxy, and fluoro; or (vi) B and B' taken together form a fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, each of said fluoren-9-xylidene substituents being selected from the group consisting of $C_1$–$C_3$ alkyl, $C_1$–$C_3$ alkoxy, fluoro and chloro.

3. The naphthopyran of claim 2 wherein, (a) $R_1$ and $R_2$ are each hydrogen, $C_1$–$C_3$ alkyl, $C_3$–$C_5$ cycloalkyl, phenyl, mono- or di-substituted phenyl, benzyl or mono-substituted benzyl, each of said phenyl and benzyl group substituents being $C_1$–$C_3$ alkyl or $C_1$–$C_3$ alkoxy;

(b) $R_3$ and $R_4$ are selected from the group consisting of $C_1$–$C_3$ alkyl and $C_1$–$C_3$ alkoxy, and m and n are each the integer 0, 1, or 2; and (c) B and B' are each selected from the group consisting of phenyl, mono-, and di-substituted phenyl, unsubstituted, mono-, and di-substituted aromatic heterocyclic groups furanyl, benzofuran-2-yl, thienyl, and benzothien-2-yl, each of said phenyl and aromatic heterocyclic substituents being selected from the group consisting of hydroxy, phenyl($C_1$–$C_3$)alkyl, $C_1$–$C_3$ alkyl, $C_1$–$C_3$ alkoxy, fluoro and chloro and the group represented by the following graphic formula:

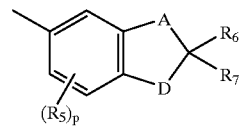

wherein A is carbon and D is oxygen, $R_5$ is $C_1$–$C_3$ alkyl or $C_1$–$C_3$ alkoxy, $R_6$ and $R_7$ are each hydrogen or $C_1$–$C_3$ alkyl, and p is the integer 0 or 1; or B and B' taken together form fluoren-9-ylidene, adamantylidene, bornylidene, norbornylidene, or bicyclo(3.3.1)nonan-9-ylidene.

4. A naphthopyran compound selected from the group consisting of:

(a) 3,3-bis(4-methoxyphenyl)-13-oxo-3,13-dihydrobenzo(b)pyrano-[4',3':6,7]naphtho(2,1-b)pyran;

(b) 2-phenyl-2-(4-methoxyphenyl)-7-oxo-2,7-dihydrobenzo(b)pyrano[4',3':5,6]naphtho(2,1-b)pyran;

(c) 2,2-diphenyl-7-oxo-2,7-dihydrobenzo(b)pyrano-[4',3':5,6]naphtho(2,1-b)pyran;

(d) 3,3-diphenyl-10-oxo-3,10-dihydrobenzo(c)pyrano-[4',3':3,4]naphtho(1,2-b)pyran;

(e) 3,3-bis(4-methoxyphenyl)-10-oxo-3,10-dihydrobenzo(c)pyrano[4',3':3,4]naphtho(1,2-b)pyran;

(f) 3,3-bis(4-methoxyphenyl)-10,10-dimethyl-3,10-dihydrobenzo(c)pyrano[4',3':3,4]naphtho(1,2-b)pyran;

(g) 3-(4-methoxyphenyl)-3-(4-morpholinophenyl)-10-oxo-3,10-dihydrobenzo(c)pyrano[4',3':3,4]naphtho(1,2-b)pyran;

(h) 3,3-diphenyl-9-oxo-3,9-dihydrobenzo(b)pyrano[4',3':3,4]naphtho(1,2-b)pyran; and (i) 3-(4-methoxyphenyl)-3-phenyl-9-oxo-3,9-dihydrobenzo(b)pyrano[4',3':3,4]naphtho(1,2-b)pyran.

5. A photochromic article comprising a polymeric organic host material and a photochromic amount of the naphthopyran compound of claim 1.

6. The photochromic article of claim 5 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of bis(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers, alkoxylated polyhydric alcohol acrylate monomers, styrene monomers, urethane acrylate monomers, glycidyl acrylate monomers, glycidyl methacrylate monomers and diallylidene pentaerythritol monomers.

7. The photochromic article of claim 6 wherein the polymeric organic host material is a solid transparent polymer selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane, polythiourethane, and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers.

8. The photochromic article of claim 7 wherein the photochromic compound is present in an amount of from 0.05 to 2.0 milligram per square centimeter of organic host material surface to which the photochromic substance(s) is incorporated or applied.

9. The photochromic article of claim 7 wherein the transparent polymer is an optical element.

10. The photochromic article of claim 9 wherein the optical element is a lens.

11. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane, polythiourethane, and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of the naphthopyran compound of claim 3.

12. A photochromic article comprising a polymerizate of an optical organic resin monomer and a photochromic amount of the naphthopyran compound of claim 1.

13. The photochromic article of claim 12 wherein the polymerizate is an ophthalmic lens or a contact lens.

14. The photochromic article of claim 12 wherein the refractive index of the polymerizate is from 1.48 to about 1.75.

15. A photochromic article comprising, in combination, a solid transparent polymeric organic host material, and a photochromic amount of each of (a) at least one naphthopyran compound of claim 1, and (b) at least one other organic photochromic compound having at least one activated absorption maxima within the range of between 400 and 700 nanometers.

16. The photochromic article of claim 15 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of bis(allyl carbonate) monomers, polyfunctional acrylate monomers, polyfunctional methacrylate monomers, diethylene glycol dimethacrylate monomers, ethoxylated bisphenol A dimethacrylate monomers, diisopropenyl benzene monomers, ethylene glycol bismethacrylate monomers, poly(ethylene glycol) bismethacrylate monomers, ethoxylated phenol bismethacrylate monomers, alkoxylated polyhydric alcohol acrylate monomers, styrene monomers, urethane acrylate monomers, glycidyl acrylate monomers, glycidyl methacrylate monomers and diallylidene pentaerythritol monomers.

17. The photochromic article of claim 16 wherein the polymeric organic host material is a solid transparent homopolymer or copolymer selected from the group consisting of poly(methyl methacrylate), poly(ethylene glycol bis-methacrylate), poly(ethoxylated bisphenol A dimethacrylate), thermoplastic polycarbonate, poly(vinyl acetate), polyvinylbutyral, polyurethane, polythiourethane, and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers.

18. The photochromic article of claim 15 wherein the organic photochromic compound (b) is selected from the group consisting of other naphthopyrans, chromenes, oxazines, metal-dithizonates, fulgides and fulgimides.

19. The photochromic article of claim 18 wherein the total amount of photochromic compound present is from 0.05 to 2.0 milligram per square centimeter of organic host material surface to which the photochromic substance(s) is incorporated or applied.

20. The photochromic article of claim 15 wherein said transparent polymeric organic host material is an optical element.

21. The photochromic article of claim 20 wherein said optical element is an ophthalmic lens or contact lens.

22. A photochromic article comprising, in combination, a polymeric organic host material and on at least one surface thereof, a cured coating of a coating composition having a photochromic amount of the naphthopyran compound of claim 1.

23. The photochromic article of claim 22 wherein the cured coating further comprises a photochromic amount of at least one other organic photochromic compound having at least one activated absorption maxima within the range of between 400 and 700 nanometers.

* * * * *